(12) United States Patent
Chamberlain et al.

(10) Patent No.: US 10,018,610 B1
(45) Date of Patent: Jul. 10, 2018

(54) MEASURING TOTAL ALKALINITY IN A RECIRCULATING FLUID SYSTEM

(71) Applicant: BECS Technology, Inc., St. Louis, MO (US)

(72) Inventors: Roger Chamberlain, Creve Coeur, MO (US); Chris Edmiston, Fairview Heights, IL (US); Brett Steinbrueck, St. Louis, MO (US); Don Williams, High Ridge, MO (US)

(73) Assignee: BECS TECHNOLOGY, INC., St. Louis, MO (US)

( * ) Notice: Subject to any disclaimer, the term of this patent is extended or adjusted under 35 U.S.C. 154(b) by 0 days.

(21) Appl. No.: 15/438,391

(22) Filed: Feb. 21, 2017

(51) Int. Cl.
*G01N 33/18* (2006.01)
*G01N 31/16* (2006.01)
*G01N 31/22* (2006.01)

(52) U.S. Cl.
CPC ........... *G01N 33/18* (2013.01); *G01N 31/166* (2013.01); *G01N 31/221* (2013.01); *G01N 33/1813* (2013.01)

(58) Field of Classification Search
CPC .... G01N 31/16; G01N 31/166; G01N 31/221; G01N 33/18; G01N 33/1813
USPC ............................ 436/39, 163; 422/75, 82.12
See application file for complete search history.

(56) References Cited

U.S. PATENT DOCUMENTS

| | | | | |
|---|---|---|---|---|
| 5,389,546 | A | * | 2/1995 | Becket ................ G01N 31/164 422/75 |
| 2006/0234389 | A1 | * | 10/2006 | Byrne ................ G01N 21/0303 436/163 |
| 2009/0200245 | A1 | * | 8/2009 | Steinbrueck ............ C02F 1/008 210/741 |
| 2017/0248568 | A1 | * | 8/2017 | Yizhack ................ G01N 33/18 |

OTHER PUBLICATIONS

Li et al. Environmental Science and Technology, vol. 47, Aug. 22, 2013, pp. 11139-11146.*

* cited by examiner

*Primary Examiner* — Maureen Wallenhorst
(74) *Attorney, Agent, or Firm* — Bryan Cave Leighton Paisner LLP

(57) ABSTRACT

A method for determining the total alkalinity (TA) in a recirculating water system without adversely impacting the pH of the water includes the steps of selecting a pH threshold ($Th_{pH}$), measuring the flow rate of the moving body of water ($f_S$), controllably adding a known amount of acid to the recirculating water system at an acid flow rate ($f_A$), repetitively measuring the pH of the recirculating water system downstream from the addition of the acid, and computing the total alkalinity of the recirculating water system when the pH measurement falls below the pH threshold.

18 Claims, 2 Drawing Sheets

MEASURING TOTAL ALKALINITY IN A RECIRCULATING FLUID SYSTEM

FIELD OF THE INVENTION

This invention relates generally to methods and systems for measuring the total alkalinity in a recirculating fluid system and, more particularly, measuring total alkalinity of flowing water in a swimming pool without adversely impacting the pH of the water.

BACKGROUND OF THE INVENTION

Managing the level of pH is a critical component of maintaining water chemistry, particularly in aquatic applications such as swimming pools, water parks, spas and the like. Among the reasons is that pH determines the effectiveness of the chlorine used to treat the water. The type of chlorine also impacts both pH and total alkalinity because different types of chlorine have very different pH levels. Low pH can cause damage to pool liners and etching of plaster, corrosion of metal components in and around the pool, and skin and eye damage. On the other hand, high pH water can cause scale formation, metal stains, cloudy water, poor efficiency of chlorine, and also can cause skin and eye irritation.

Unlike pH—which is basically a scale to measure against—total alkalinity is a measurement of all alkaline substances dissolved in the water. These substances are primarily hydroxides, carbonates and bicarbonates, along with a few others. These alkaline substances buffer pH in the water. In other words, total alkalinity is a measurement of the water's ability to resist change in pH. Having the right level of total alkalinity aids in keeping the pH level stabilized.

The total alkalinity of a body of water is normally measured through a titration process. Starting with a known volume of the water to be tested, a strong acid is added (typically one calibrated a drop at a time), mixing as necessary, until the pH falls to a specified value. Using the known initial volume of water and the known volume of added acid, one can compute the total alkalinity using conventional calculations.

This conventional method works well for a still body of water. However, in certain applications, including most aquatic applications, specifically a recirculating water system, the total alkalinity for a flowing stream of water is required.

When the water is recirculated, as in aquatic applications, special care must be taken in performing the alkalinity measurement. Adding a strong acid to a recirculating system for the purpose of measuring alkalinity can adversely affect the pH of the entire body of water, especially in small bodies of water such as spas and slash pads.

SUMMARY OF THE INVENTION

According to one aspect of the present invention, a method for determining the total alkalinity (TA) in a recirculating water system includes the steps of selecting a pH threshold ($Th_{pH}$), measuring the flow rate of the moving body of water ($f_S$), controllably adding a known amount of acid to the recirculating water system at an acid flow rate ($f_A$), repetitively measuring the pH of the recirculating water system downstream from the addition of the acid, and computing the total alkalinity of the recirculating water system when the pH measurement falls below the pH threshold. The total alkalinity may be computed as $TA = K_{CAL} \cdot (f_A/f_S)$, where $K_{CAL}$ is a calibration constant.

The step of controllably adding a known amount of acid to the recirculating water system can be accomplished in a number of ways, including, adding acid at an initial acid flow rate ($f_{A, INIT}$) and, until the pH measurement falls below the pH threshold, repetitively waiting a period of time, measuring the pH of the recirculating water system, and increasing the acid flow rate by a fixed increment. An alternative method for controllably adding acid to the recirculating water system includes adding acid at an initial acid flow rate ($f_{A, INIT}$), monitoring the measured pH until the measured pH exhibits an exponential response, and extrapolating a stable pH reading based on the exponential response.

Another embodiment includes a method for determining the calcium saturation index of a body of water, wherein at least a portion of the body of water is flowing, using the steps of measuring, by a master controller, the pH, temperature, and total dissolved solids of the body of water, determining, in a location remote from the master controller, the total alkalinity (TA) of the flowing portion of water, manually determining the calcium hardness of the body of water, and calculating the calcium saturation index of the body of water based on the pH, temperature, total dissolved solids, calcium hardness of the body of water, and the total alkalinity of the flowing portion of water. In this embodiment, the determination of TA may include selecting a pH threshold ($Th_{pH}$), measuring the flow rate of the flowing portion of water ($f_S$), controllably adding acid to the flowing portion of water at an acid flow rate ($f_A$), repetitively measuring the pH of the flowing portion of water downstream from the addition of the acid, and computing the total alkalinity of the flowing portion of water when the pH measurement falls below the pH threshold. The total alkalinity may be computed as: $TA = K_{CAL} A (f_A/f_S)$, where $K_{CAL}$ is a calibration constant.

BRIEF DESCRIPTION OF THE FIGURES

These and other features, aspects and advantages of the invention will become more fully apparent from the following detailed description, appended claims, and accompanying drawings, wherein the drawings illustrate features in accordance with an exemplary embodiment of the present invention, and wherein:

DETAILED DESCRIPTION OF THE INVENTION

Figure 1:
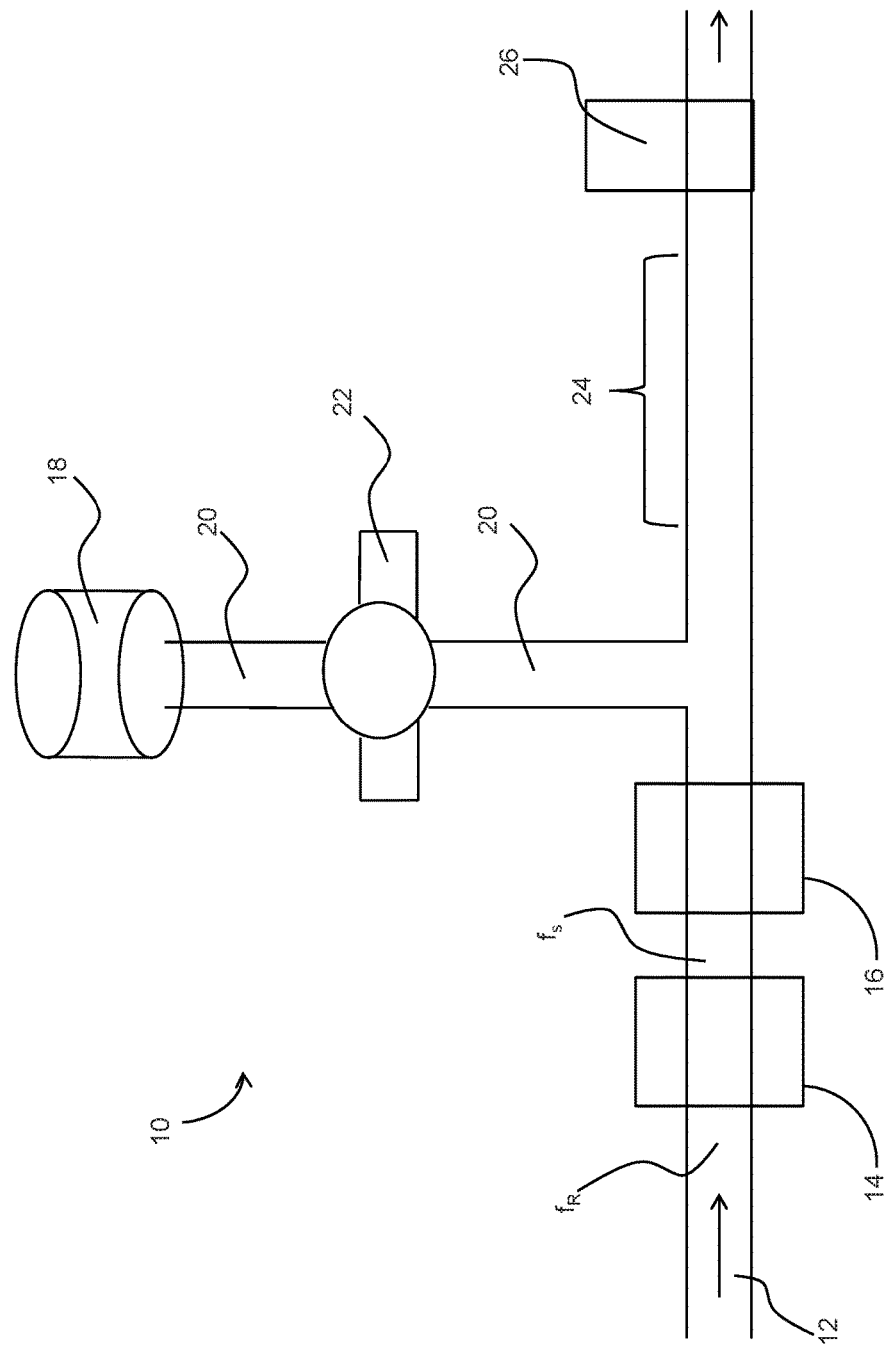
FIG. 1 is a block diagram illustrating the principal components of an embodiment of the system for determining the total alkalinity of a flowing body of fluid.
Figure 2:
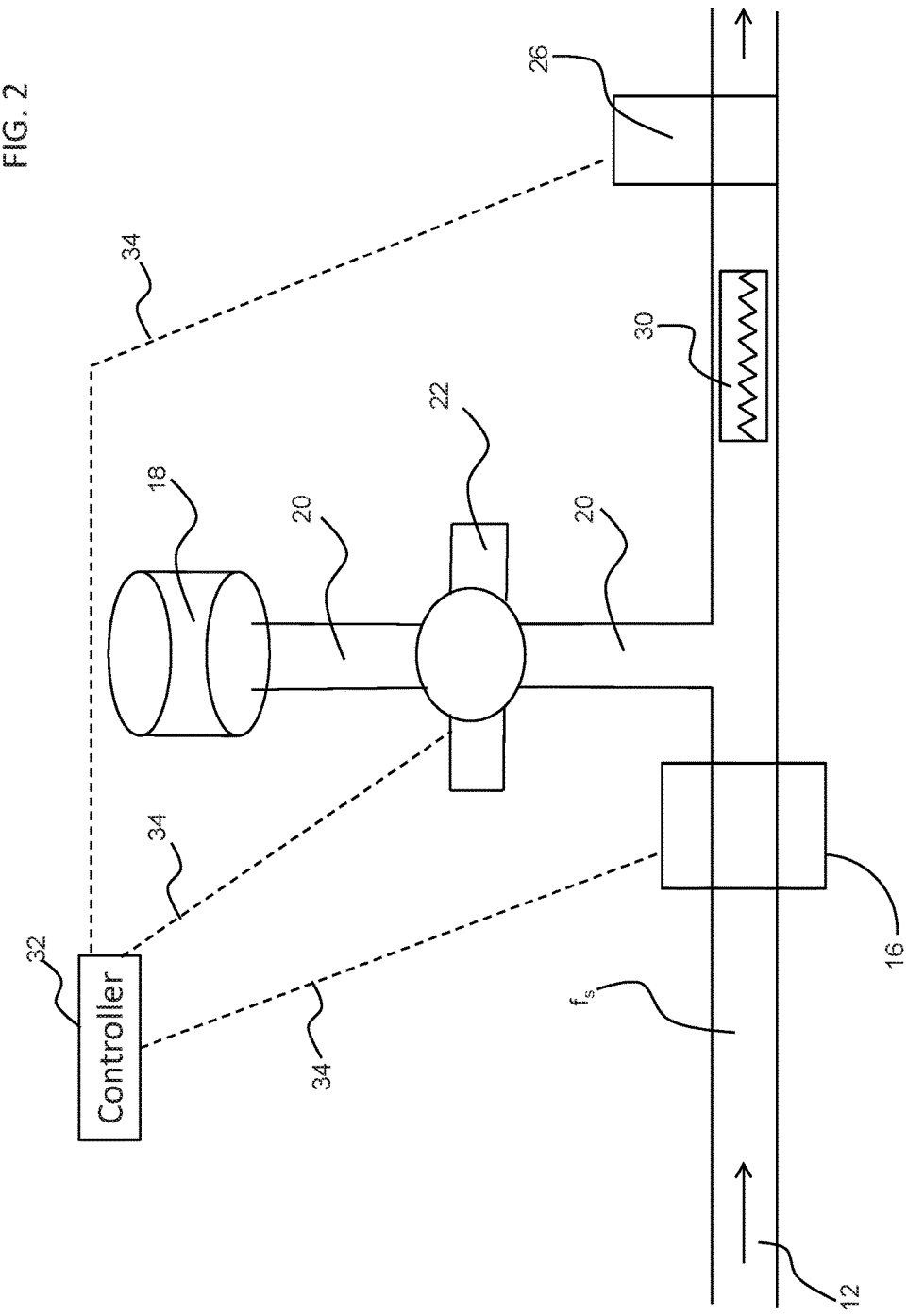
FIG. 2 is a block diagram illustrating the principal components of another embodiment of the system for determining the total alkalinity of a flowing body of fluid.

Referring to FIGS. 1 and 2, the principle components of a system 10 for determining the total alkalinity of a recirculating water system are illustrated. The system 10 may be used in connection with the operation of any form of aquatic facility, for example, a family water recreation facility that may include features such as a swimming pool, a spa, whirlpool, and other features such as water jets, water slides, river rapid rides, waterfalls, decorative fountains, spillways, buckets, lazy rivers, and the like. The system and the methods described below allow one to modify the standard titration technique using fixed volumes of water to calculate total alkalinity with known flow rates in a flowing stream.

In one embodiment illustrated in FIG. 1, the system 10 includes tubing 12 for at least a sample of the water to be analyzed to flow, a flow rate regulator 14 that can alter the flow rate of the water, and a flow rate meter 16 for measuring the water flow rate. A second section of tubing 20 is coupled to the tubing 12 downstream of the flow rate meter 16. An acid, for example muriatic acid stored in vessel 18, flows into the stream of water as controlled by a precision metering pump 22, which pumps at a set rate $f_A$. The stream of water and the added acid are combined in a mixing section 24 configured to ensure adequate mixing downstream from the intersection of tubing 12 and the second section of tubing 20. The system further includes a pH probe 26 to measure the acidity of the stream of water. Certain of these components may be controlled by a computer-based controller 32 as shown in FIG. 2. Thus, the flow rate meter 16 and the pH probe 26 may send signals to the controller 32 that represent the flow rate and the pH of the flowing water respectfully. The controller 32 may send a signal to the pump 22 to control the addition of acid to the flowing water.

The sample stream of water to be measured enters the tubing 12 from the left end as depicted in FIGS. 1 and 2. As needed, the flow rate regulator 14 regulates the flow of the water to a certain flow rate $f_R$. The flow rate of the stream of water, $f_S$, is then measured by the flow rate meter 16. If $f_S < f_R$, there is insufficient pressure differential above and below the flow regulator 14 for it to operate effectively. An alternative approach is to monitor the sample stream flow rate (instead of including a flow regulator) and to not perform an alkalinity reading if the sample stream flow rate is not in an appropriate range.

The muriatic acid to be added is fed via precision metering pump 22, which may be set by the controller 32. The combination of the sample stream and the added acid flow into the mixing section 24 configured to ensure adequate mixing. The mixing section 24 may include mechanical elements to create turbulence to mix the sample stream and the acid. Optionally, a mixer 30, such as an auger created on a 3D printer, can be included in this length of tubing 24. Downstream of the mixing, the pH of the stream is measured by the pH probe 26 and a signal indicative of the pH is sent to the controller 32.

Preferably, the muriatic acid is sufficiently strong as to have a pH below the threshold chosen below. The concentration used for calibration is preferably maintained for subsequent readings; however, the specific concentration is not crucial, as long as there is sufficient controllability of flow rates by the metering pump 22, and the concentration is consistent between the calibration and the later readings by the pH probe 26.

The operation of performing a reading of the total alkalinity may now be described. First, a pH threshold is chosen, preferably between 4.0 and 5.0 pH. This threshold value is labeled $Th_{pH}$. The metering pump 22 precisely controls the delivery of acid at a rate that takes the pH reading at or just below $Th_{pH}$. There are a number of possible methods to accomplish this as described below.

When the pH reading is at or just below $Th_{pH}$, the sample flow rate $f_S$ and the acid flow rate $f_A$ are recorded by the controller 32. The total alkalinity (TA) may then be computed as follows:

$$TA = K_{CAL} \times \left(\frac{f_A}{f_S}\right),$$

where $K_{CAL}$ is a calibration constant defined below.

The determination of the calibration constant $K_{CAL}$ preferably uses the inverse of the above equation. The method includes recording $f_S$ and $f_A$. The total alkalinity is measured using an independent method, for example, a color test method or other suitable conventional method. The calibration constant, $K_{CAL}$, may then be computed as $$K_{CAL} = TA \times \left(\frac{f_S}{f_A}\right).$$

In many uses, the systems and methods described herein are used in conjunction with a large aquatic facility, such as a municipal swimming pool or water park. The aquatic facility many include a master controller such as a BECSys 7 controller commercially available through BECS Technology, Inc. of St. Louis, Mo. As is known in the industry, the master controller may measure the pH, temperature, and total dissolved solids of the water in the aquatic facility, as well as control the discharge of chemicals into the water. The components illustrated in FIGS. 1 and 2 preferably may be located remote from the master controller. The calibration of the pH reading can take advantage of the fact that the pH in the sample stream with the acid pump off (i.e., not delivering any acid) will be approximately equal to the pH of the water in the vicinity of the master controller. As such, the local pH calibration can be tied to the pH reading of the master controller. This can be accomplished via any traditional, single-point calibration technique, in which the individual reading used for calibration (which comes from the master controller) is used to adjust either the slope or the offset of a linear calibration.

For example, when reading a sensor with a linear response, the transformation function (i.e., the conversion function) may have the following form: pHval=m×ADCval+b, where ADCval is the input value from an analog-to-digital converter, pHval is the value of the current pH reading (corresponding to the input ADCval), m is the conversion slope, and b is the offset of the conversion. Single point calibration of the slope uses an independent pH reading (e.g., from the master controller), $pHval_{CAL}$, a current analog-to-digital converter input value, $ADCval_{CAL}$, and b to compute a new (calibrated) slope:

$$m = \frac{pHval_{CAL} - b}{ADCval_{CAL}}.$$

Single point calibration of the offset uses an independent pH reading (e.g., from the master controller), $pHval_{CAL}$, a current analog-to-digital converter input value, $ADCval_{CAL}$, and m to compute a new (calibrated) offset: $b = pHVal_{CAL} - m \times ADCval_{CAL}$.

During either a reading or a calibration, the controller 32 preferably controls the acid pump so as to deliver acid at a rate that takes the pH reading at or just below $Th_{pH}$. This may be accomplished in a number of ways to avoid adversely impacting the pH of the body of water. In a first method, a linear progression technique starts at a fixed (slow) pump rate, $f_{A,INT}$. After waiting a sufficient time for the pH reading to stabilize, for example, about 120 seconds, the pH value is read by the controller 32. If the pH reading is $\leq Th_{pH}$, then $f_A$ is set to the current pump rate. If the pH reading is greater than $Th_{pH}$, the pump rate is increased by a fixed increment, $f_{A,INC}$, and the process returns back to waiting a sufficient time for the pH reading to stabilize and reading the pH value.

Another embodiment includes steps to determine when the pH reading has stabilized. This embodiment includes comparing the difference between two successive pH readings and, when the difference falls below a chosen difference threshold for a set duration of time, setting $f_A$ equal to the acid flow rate at that time. This embodiment would include selecting a difference threshold, for example 0.01 pH, and selecting the set duration of time, for example, 20 seconds.

An alternative technique is a fast linear progression, in which the pH probe 26 reads the pH at a higher sampling rate. The process waits a sufficient time for the exponential response of the pH measurement to become evident in the pH samples. The stable pH reading is extrapolated from the initial exponential curve in the pH samples. If the stable pH reading is s $Th_{pH}$, then $f_A$ is set to the current pump rate. If the stable pH reading is greater than $Th_{pH}$, the pump rate is increased by a fixed increment, $f_{A,INC}$, and the process returns back to waiting a sufficient time for the exponential response of the pH measurement to become evident in the pH samples, and extrapolating the pH value.

For example, a system with an exponential time response can be expressed using the following formula: $val(t)=val_F + (val_{INIT}-val_F) \times e^{-(t/\tau)}$, where $val_{INIT}$ is the initial value, $val_F$ is the final value, and T is the time constant of the system (pH probe in our case). By taking several readings of $val(t)$, appropriate software can perform a least mean squares curve fit to the above equation, for the purpose of estimating the final value $V_F$.

A third method for controlling the delivery of acid is a binary progression technique. The sequence of steps is the same as for linear progression, except instead of a regular increment in the acid pump rate, $f_{A,INC}$, the pump rate follows a binary search pattern. For example, two values may be initialized to the minimum, $f_{A,MIN}$, and maximum, $f_{A,MAX}$, acid feed rates supported by the pump (or alternatively, some narrower search range). The acid feed rate $f_A$ is set to the mid-point between $f_{A,MIN}$ and $$f_{A \cdot MAX} : f_A = \frac{f_{A \cdot MIN} + f_{A \cdot MAX}}{2}.$$

Then, the pH reading (either value at end of delay period or extrapolated from exponential response) is compared to threshold $Th_{pH}$. If the pH value is within a tolerance, $\varepsilon$, of the threshold (e.g., $Th_{pH}-\varepsilon \le pHval \le Th_{pH}+\varepsilon$), the current feed rate $f_A$ is the feed rate to use to compute total alkalinity. Otherwise, if the pH value is above threshold, set $f_{A,MIN} \leftarrow f_A$ and the process returns to comparing the pH reading. Otherwise, if the pH value is below threshold, set $f_{A,MAX} \leftarrow f_A$ and the process returns to comparing the pH reading. This preferably results in a faster search to find the value of acid feed rate that is near threshold.

In each of the above approaches to controlling the acid, if the pH falls below a lower threshold ($Th_{pHlow}$) before the time period is complete, the reading can be considered finished (with a pH value of $Th_{pHlow}$) A reasonable value for $Th_{pHlow}$ is 4.0.

For a traditional titration process, the volume of water used for the titration is fixed, and although it ends up with a low pH (and therefore must be disposed of safely), it is sufficiently small that simple dilution is fairly easy (e.g., returning it to the pool). For a titration process with flowing water, the volume of water affected by the added acid is potentially much larger, but preferably, the total acid added is small enough that it does not impact the overall pool chemistry. The above-described methods for controlling the delivery of acid, particularly the fast linear progression and binary progression techniques, minimize the overall quantity of acid used to perform the titration.

Another approach to minimizing the impact on pool chemistry is to lower the frequency of the total alkalinity readings (e.g., read alkalinity only once per day, when the pool is closed, to give time for the system to recover from any inadvertent impact). This has a potential to have a detrimental effect on the total alkalinity control, as fewer readings means less knowledge of the current state of the water chemistry while making control decisions (i.e., the total alkalinity control decisions described above).

Yet another approach to minimizing the impact on pool chemistry is to control the timing of the flowing water titration process. For example, the water chemistry controller detects when the pH of the system is high (i.e., above setpoint), and can feed acid to lower the pH in the controlled body of water. This would be an ideal time to perform a flowing water titration, as the titration adds acid as well, and has the benefit of improving system visibility for control purposes.

There are a number of benefits to the automated sensing of alkalinity that accrue to the master controller of the aquatic facility that has overall responsibility for water chemistry. For example, monitoring the chemistry in an aquatic facility is aided when one knows the calcium saturation index (CSI) of the water, which is a measure of the pool water's tendency to scale or corrode. The input factors that determine the saturation index include pH, temperature, total dissolved solids, total alkalinity, and calcium hardness. Prior to the availability of the total alkalinity reading, the master controller was able to directly measure pH, temperature, and total dissolved solids, while the pool operator was required to manually input the values for total alkalinity and calcium hardness. With the availability of a total alkalinity reading, one of the manual steps required has been eliminated, both lowering labor requirements and increasing accuracy (as manual testing of total alkalinity is an error-prone process).

The master controller preferably has means for reporting its readings both locally and remotely (to remote devices via the Internet). This includes establishing and reporting on out-of-range conditions (i.e., alarms) on these readings. By adding total alkalinity to this set, the ability of pool operators to both understand the chemical state of the pool and to be informed when something is amiss is improved.

While the above description is primarily focused on reading the total alkalinity, it is also desirable to control the alkalinity in a body of water. One approach to alkalinity control is to alter the mechanism for pH control depending upon the alkalinity reading.

There are two mechanisms commonly used for pH control, and many systems have both installed. One is via feeding of carbon dioxide ($CO_2$), and the other is via feeding acid. Generally, feeding $CO_2$ will leave alkalinity unchanged, and feeding acid can lower alkalinity. One preferred approach follows this logic. If alkalinity is above a given threshold (which may be set by the user), pH is controlled by adding acid. Alternatively, if alkalinity is below the threshold, pH is preferably controlled by adding $CO_2$. Yet another preferred embodiment is to proportion the control pH by prorating the addition of $CO_2$ and acid.

A second approach to alkalinity control is to support the feeding of sodium bicarbonate, which has the tendency to raise the alkalinity of the water. The feeding of sodium bicarbonate provides an increase in alkalinity, and the feeding of acid provides a decrease in alkalinity.

Yet another approach is to adjust the mechanism for chlorine control as a mechanism for alkalinity control. Different types of chlorine feed drive alkalinity up vs. down, and similar to the pH control example above, one can adjust the proportion of chlorine feed via one mechanism or another to actively push alkalinity towards its desired range of operation.

In addition to being able to control the alkalinity in a pool, knowledge of the alkalinity can benefit other aspects of the water chemistry control. For example, when alkalinity is very low, the pH is dramatically more sensitive to acid injection, which can motivate the alteration of control parameters (for example, feed slower to reduce overshoot). Similarly, when the alkalinity is very high, the opposite occurs, pH is dramatically less sensitive to acid injection. As a result, one can alter control parameters in the opposite direction (feed acid at a greater rate for pH control).

Although certain illustrative embodiments and methods have been disclosed herein, it will be apparent from the foregoing disclosure to those skilled in the art that variations and modifications of such embodiments and methods may be made without departing from the spirit and scope of the invention. Accordingly, it is intended that the invention should be limited only to extent required by the appended claims and the rules and principals of applicable law.

The invention claimed is:

1. A method for determining a total alkalinity (TA) of a recirculating water system comprising the steps of:
    (a) selecting a first pH threshold ($Th_{pH}$);
    (b) measuring a flow rate of the recirculating water system ($f_S$);
    (c) controllably adding a known amount of acid to the recirculating water system at an acid flow rate ($f_A$);
    (d) repetitively measuring the pH of the recirculating water system downstream from the addition of the acid; and
    (e) computing the total alkalinity of the recirculating water system when the pH measurement falls below the first pH threshold, wherein the total alkalinity is computed as: $TA = K_{CAL} \cdot (f_A/f_S)$, wherein $K_{CAL}$ is a calibration constant.

2. The method of claim 1 wherein $K_{CAL}$ is defined by $TA_{CAL} \cdot (f_S/f_A)$ and wherein $TA_{CAL}$ is a measured total alkalinity reading using a method independent from the computation of total alkalinity in step (e).

3. The method of claim 1 wherein the step of controllably adding acid to the recirculating water system comprises the steps of:
    adding acid at an initial acid flow rate ($f_{A, INIT}$); and
    until the pH measurement falls below the first pH threshold, repetitively:
        measuring the pH of the recirculating water system; and
        increasing the acid flow rate by a fixed increment; and
    setting $f_A$ equal to the acid flow rate when the pH measurement falls below the first pH threshold for computing the total alkalinity of the recirculating water system.

4. The method of claim 3 further comprising:
    selecting a second pH threshold that is less than the first DH threshold; and
    if the measured pH falls below the second pH threshold, setting $f_A$ equal to the acid flow rate when the pH measurement falls below the second pH threshold for computing the total alkalinity of the recirculating water system.

5. The method of claim 1 wherein the step of controllably adding acid to the recirculating water system comprises the steps of:
    selecting a third pH threshold;
    selecting a duration of time;
    adding acid at an initial acid flow rate ($f_{A, INIT}$);
    calculating a difference between two successive pH measurements; and
    until the difference between two successive pH measurements falls below the third pH threshold for the set duration of time, repetitively:
        measuring the pH of the recirculating water system; and
        increasing the acid flow rate by a fixed increment; and
    setting $f_A$ equal to the acid flow rate for computing the total alkalinity of the recirculating water system when the difference between two successive pH measurements falls below the third pH threshold for the set duration of time.

6. The method of claim 5 further comprising:
    selecting a second DH threshold that is less than the first DH threshold; and
    if the measured pH falls below the second pH threshold, setting $f_A$ equal to the acid flow rate when the pH measurement falls below the second pH threshold for computing the total alkalinity of the recirculating water system.

7. The method of claim 1 wherein the step of controllably adding acid to the recirculating water system comprises the steps of:
    (a) adding acid at an initial acid flow rate ($f_{A, INIT}$);
    (b) monitoring the measured pH until the measured pH exhibits an exponential response; and
    (c) extrapolating a stable pH reading based on the exponential response.

8. The method of claim 7 further comprising:
    selecting a second pH threshold that is less than the first pH threshold; and
    if the measured pH falls below the second pH threshold, setting $f_A$ equal to the acid flow rate when the pH measurement falls below the second pH threshold for computing the total alkalinity of the recirculating water system.

9. The method of claim 1 wherein acid is controllably added using a pump having a maximum and a minimum feed rate; and wherein the step of controllably adding acid to the recirculating water system comprises the steps of:
    selecting a tolerance of the first pH threshold;
    adding acid at an acid flow rate wherein the acid flow rate is set to about an average of the maximum and minimum feed rates and, until the pH measurement is within the tolerance of the pH threshold, repetitively:
        comparing the measured pH of the recirculating water system to the selected first pH threshold;
        if the measured pH is above the first pH threshold, revising the minimum feed rate to the current acid flow rate;
        if the measured pH is below the first pH threshold, revising the maximum feed rate to the current acid flow rate; and
        resetting the acid flow rate to about the average of the revised maximum and minimum feed rates.

10. The method of claim 9 further comprising:
selecting a second pH threshold that is less than the first pH threshold; and
if the measured pH falls below the second pH threshold, setting $f_A$ equal to the acid flow rate when the pH measurement falls below the second pH threshold for computing the total alkalinity of the recirculating water system.

11. The method of claim 1 wherein the first DH threshold ($Th_{pH}$) is selected between about 4.0 and about 5.0 pH.

12. The method of claim 1 further comprising the steps of:
selecting a total alkalinity threshold;
controlling the pH of the recirculating water system by either:
feeding additional acid to the recirculating water system if the computed total alkalinity is above the total alkalinity threshold; or
feeding carbon dioxide to the recirculating water system if the computed total alkalinity is below the total alkalinity threshold.

13. The method of claim 1 further comprising the steps of:
selecting a total alkalinity threshold; and
controlling the pH of the recirculating water system by:
feeding additional acid to the recirculating water system; and
feeding an amount of carbon dioxide to the recirculating water system,
wherein the amount of acid and the amount of carbon dioxide fed is selected based on a relationship between the computed total alkalinity and the total alkalinity threshold.

14. The method of claim 1 further comprising the steps of:
selecting a total alkalinity threshold;
feeding additional acid to the recirculating water system; and
feeding an amount of sodium bicarbonate to the recirculating water system,
wherein the amount of acid and the amount of sodium bicarbonate fed is selected based on a relationship between the computed total alkalinity and the total alkalinity threshold.

15. The method of claim 1 further comprising the steps of:
selecting a total alkalinity threshold;
feeding an amount of acid to the recirculating water system; and
feeding an amount of chlorine to the recirculating water system,
wherein the amount of acid and the amount of chlorine fed is selected in part based on a relationship between the computed total alkalinity and the total alkalinity threshold.

16. A method for determining a calcium saturation index of water within a recirculating system, wherein at least a portion of the water is flowing, comprising the steps of:
measuring, by a master controller, the pH, temperature, and total dissolved solids of the water within the recirculating system;
determining, in a location remote from the master controller, a total alkalinity (TA) of the flowing portion of water, wherein the determination of TA comprises the steps of:
selecting a pH threshold ($Th_{pH}$);
measuring a flow rate of the flowing portion of water ($f_S$);
controllably adding acid to the flowing portion of water at an acid flow rate ($f_A$);
repetitively measuring a pH of the flowing portion of water downstream from the addition of the acid; and
computing the total alkalinity of the flowing portion of water when the pH measurement falls below the pH threshold, wherein the total alkalinity is computed as: $TA=K_{CAL} \cdot (f_A/f_S)$, wherein $K_{CAL}$ is a calibration constant;
manually determining a calcium hardness of the water; and
calculating the calcium saturation index of the water within the recirculating system based on the pH, temperature, total dissolved solids, and calcium hardness of the water within the recirculating system, and the total alkalinity of the flowing portion of water.

17. The method of claim 16 further comprising the step of calibrating the measurement of the pH of the flowing portion of water based on the measurement of the pH from the master controller.

18. A system for determining a total alkalinity (TA) of water within a recirculating water system comprising:
a flow rate meter for measuring the flow rate of the recirculating water system ($f_S$);
a vessel holding acid;
a pump for controllably adding acid to the recirculating water system at an acid flow rate ($f_A$);
a probe for repetitively measuring the pH of the recirculating water system downstream from the addition of the acid; and
a computing element for computing the total alkalinity of the recirculating water system when the pH measurement falls below a pH threshold ($Th_{pH}$), wherein the total alkalinity is computed as: $TA=K_{CA} \cdot (f_A/f_S)$, and wherein $K_{CAL}$ is a calibration constant.

* * * * *